(12) United States Patent
Knauf-Beiter et al.

(10) Patent No.: US 6,552,039 B2
(45) Date of Patent: Apr. 22, 2003

(54) FUNGICIDAL COMBINATIONS COMPRISING A 4-PHENOXYQUINOLINE

(75) Inventors: Gertrude Knauf-Beiter, Müllheim (DE); Jürg Speich, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/056,383

(22) Filed: Jan. 24, 2002

(65) Prior Publication Data

US 2002/0103224 A1 Aug. 1, 2002

Related U.S. Application Data

(62) Division of application No. 09/423,701, filed as application No. PCT/EP98/02841 on May 13, 1998, now Pat. No. 6,479,511.

(51) Int. Cl.[7] ................................................ A61K 31/47
(52) U.S. Cl. ....................................................... 514/309
(58) Field of Search ......................................... 514/309

(56) References Cited

FOREIGN PATENT DOCUMENTS

| AU | 689684 B | 2/1998 |
|---|---|---|
| DE | 4444111 | 6/1996 |
| EP | 326330 | 8/1999 |

OTHER PUBLICATIONS

Tomlin, The Pesticide Manual Incorporation, The Agrochemicals Handbook, 10th Ed (1998) pp 124, 125, 268, 269, 328–330, 428–429, 514, 515, 562, 563, 580, 581, 776, 777, 942, 943, 965, 966, 1033, 1034.

*Primary Examiner*—Alton Pryor
(74) *Attorney, Agent, or Firm*—William A. Teoli, Jr.; Rose M. Allen

(57) ABSTRACT

Novel fungicidal compositions having a synergistically increased action, wherein component
a) is a 4-phenoxyquinoline of formula I

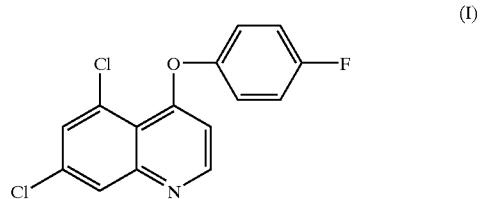

in association with
b) either an azole fungicide (II), or a morpholine fungicide (III), or a compound of formula IV (spiroxamine), or a compound of formula V (fenpropidine), or a compound of formula VI (dimethomorph), or a compound of formula VII (pyrimethanil, cyprodinil), or prochloraz.

2 Claims, No Drawings

FUNGICIDAL COMBINATIONS COMPRISING A 4-PHENOXYQUINOLINE

This Appl'n is a DIV of 09/423,701 filed Nov. 12, 1999 now U.S. Pat. No. 6,479,511, which is the national stage of PCT/EP98/02841, filed May 13, 1998.

The present invention relates to novel fungicidal compositions for the treatment of phytopathogenic diseases of crop plants, especially phytopathogenic fungi, and to a method of combatting phytopathogenic diseases on crop plants.

It is known that certain phenoxyquinoline derivatives have biological activity against phytopathogenic fungi, e.g. from EP-A-0326330 where their properties and methods of preparation are described. On the other hand azole fungicides, morpholines and aminopyrimidines are widely known as plant fungicides for application in various crops of cultivated plants. However, crop tolerance and activity against phytopathogenic plant fungi do not always satisfy the needs of agricultural practice in many incidents and aspects.

It has now been found that the use of
a) a 4-phenoxyquinoline of formula I

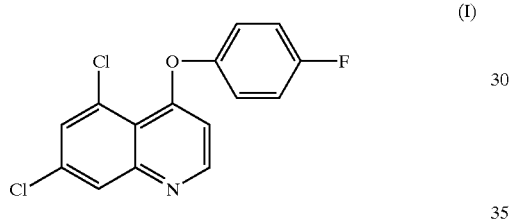

in association with
b) either an azole fungicide of formula II

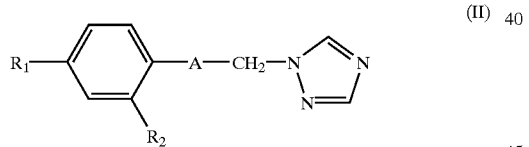

wherein
A is selected from

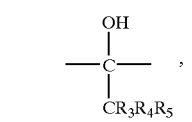 (i)

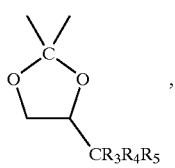 (ii)

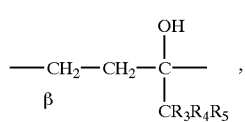 (iii)

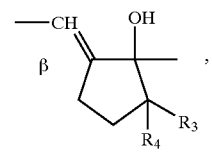 (iv)

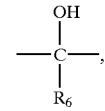 (v)

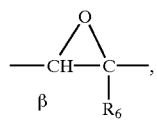 (vi)

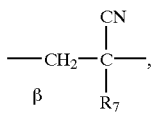 (vii)

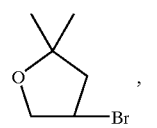 (viii)

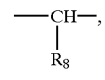 (ix)

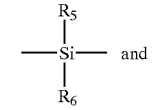 (x) and

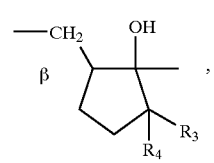 (xi)

whereby the β-carbon attaches to benzene ring of formula I, and wherein
$R_1$ is H, F, Cl, 4-fluorophenoxy or 4-chlorophenoxy;
$R_2$ is H, Cl or F;
$R_3$ and $R_4$ are independently H or $CH_3$;
$R_5$ is $C_{1-4}$alkyl or cyclopropyl;
$R_6$ is 4-chlorophenyl or 4-fluorophenyl;
$R_7$ is phenyl, and
$R_8$ is allyloxy, $C_{1-4}$alkyl, or 1,1,2,2-tetrafluoroethoxymethyl, and the salts of such azole fungicide;
or a morpholine fungicide of formula III

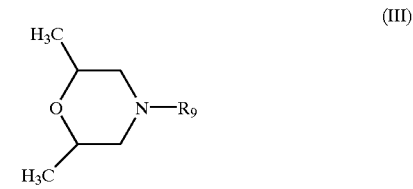

wherein
$R_9$ is $C_{8-15}$cycloalkyl, $C_{8-15}$alkyl, or $C_{1-4}$alkylphenyl-$C_{1-4}$alkyl, and the salts of such morpholine fungicide;
or a compound of formula IV

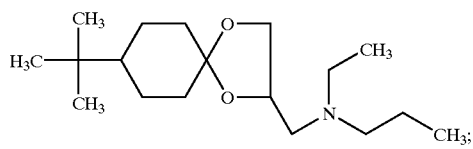

or a compound of formula V

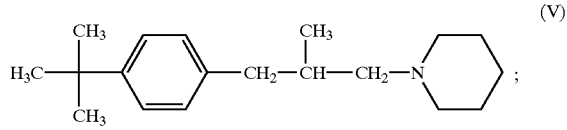

or a compound of formula VI

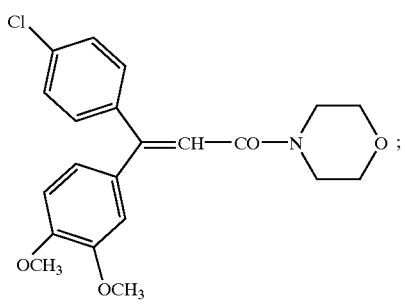

or a compound of formula VII

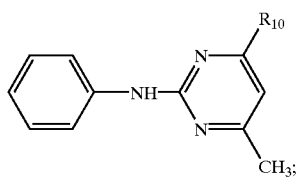

wherein $R_{10}$ is methyl or cyclopropyl;
or prochloraz;
is particularly effective in combatting or preventing fungal diseases of crop plants. These combinations exhibit synergistic fungicidal activity.

The combinations according to the invention may also comprise more than one of the active components b), if broadening of the spectrum of disease control is desired.

Salts of the azole and morpholine active ingredients are prepared by reaction with acids, e.g., hydrohalo acids such as hydrofluoric acid, hydrochloric acid, hydrobromic acid and hydroiodic acid, or sulfuric acid, phosphoric acid or nitric acid, or organic acids such as acetic acid, trifluoroacetic acid, trichloroacetic acid, propionic acid, glycolic acid, lactic acid, succinic acid, citric acid, benzoic acid, cinnamic acid, oxalic acid, formic acid, benzensulfonic acid, p-toluenesulfonic acid, methanesulfonic acid, salicylic acid, p-aminosalicylic acid and 1,2-naphtalenedisulfonic acid.

The active ingredient combinations are effective against phytopathogenic fungi belonging to the following classes: Ascomycetes (e.g. Venturia, Podosphaera, Erysiphe, Monilinia, Mycosphaerella, Uncinula); Basidiomycetes (e.g. the genus Hemileia, Rhizoctonia, Puccinia); Fungi imperfecti (e.g. Botrytis, Helminthosporium, Rhynchosporium, Fusarium, Septoria, Cercospora, Alternaria, Pyricularia and *Pseudocercosporella herpotrichoides* (Tapesia spp.)); Oomycetes (e.g. Phytophthora, Peronospora, Bremia, Pythium, Plasmopara).

Target crops for the areas of indication disclosed herein comprise within the scope of this invention e.g. the following species of plants: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). This list does not represent any limitation.

The combinations according to the present invention are particularly effective against powdery mildews and rusts, Rhynchosporium and Pyrenophora, and leptosphaeria fungi, in particular against pathogens of monocotyledoneous plants such as cereals, including wheat and barley.

The amount of combination of the invention to be applied, will depend on various factors such as the compound employed, the subject of the treatment (plant, soil, seed), the type of treatment (e.g. spraying, dusting, seed dressing), the purpose of the treatment (prophylactic or therapeutic), the type of fungi to be treated and the application time.

Particularly preferred mixing partners of the compunds of formula II are those in which $R_1$ is Cl, $R_2$ and $R_3$ are H, $R_4$ is $CH_3$ and $R_5$ is cyclopropyl and A is the moiety (i) (commonly known as cyproconazole); those wherein $R_1$ and $R_2$ are Cl, $R_3$ and $R_4$ are H, $R_5$ is propyl and A is the moiety (i) (commonly known as hexaconazole); those in which $R_1$ is 4-chlorophenoxy, $R_2$ is Cl, $R_3$, $R_4$ and $R_5$ are H and A is the moiety (ii) (commonly known as difenoconazole); those in which $R_1$ and $R_2$ are Cl, $R_3$ and $R_4$ are H, $R_5$ is ethyl and A is the moiety (ii) (commonly known as etaconazole); those in which $R_1$ and $R_2$ are Cl, $R_3$ and $R_4$ are H, $R_5$ is propyl and A is the moiety (ii) (commonly known as propiconazole); those in which $R_1$ is Cl, $R_2$ is H, $R_3$, $R_4$ and $R_5$ are $CH_3$ and A is the moiety (iii) (commonly known as tebuconazole); those in which $R_1$ is Cl, $R_2$ is H and A is the moiety (iv) (commonly known as triticonazole); those in which $R_1$ is H, $R_2$ is F, $R_6$ is 4-fluorophenyl and A is the moiety (v) (commonly known as flutriafol); those in which $R_1$ is H, $R_2$ is Cl, $R_6$ is 4-fluorophenyl and A is the moiety (vi) (commonly known as epoxiconazole); those in which $R_1$ is Cl, $R_2$ is H, $R_7$ is phenyl and A is the moiety (vii) (commonly known as fenbuconazole); those in which $R_1$ and $R_2$ are Cl, and A is the moiety (viii) (commonly known as bromuconazole); those in which $R_1$ and $R_2$ are Cl, $R_8$ is propyl and A is the moiety (ix) (commonly known as penconazole); those in which $R_1$ and $R_2$ are Cl, $R_8$ is allyloxy and A is the moiety (ix) (commonly known as imazalil); and those in which $R_1$ and $R_2$ are Cl, $R_8$ is 1,1,2,2-tetrafluoroethoxymethyl and A is the moiety (ix) (commonly known as tetraconazole); those wherein $R_1$ is F, $R_2$ is H, $R_5$ is $CH_3$, $R_6$ is 4-fluorophenyl, and A is the moiety (x) (commonly known as flusilazole); and those in which $R_1$ is chloro, $R_2$ is hydrogen, $R_3$ and $R_4$ are methyl and A is the moiety (xi) (commonly known as metconazole). From this group propiconazole, difenoconazole, penconazole and cyproconazole are of particular interest as prefered embodiments of this invention.

Particularly preferred mixing partners of the compounds of formula III are those wherein $R_8$ is cyclododecyl (commonly known as dodemorph), or $C_{10-13}$alkyl (commonly known as tridemorph), or 3-(4-tert-butylphenyl)-2-methylpropyl (commonly known as fenpropimorph). Predominantly, the cis-positioning of the methyl groups at the morpholine ring is present in the compounds of formula III when used in the combinations of the invention.

The compound of formula IV is commonly known as spiroxamine.

The compound of formula V is commonly known as fenpropidine.

The compound of formula VI is commonly known as dimethomorph.

The compounds of formula VII wherein $R_{10}$ is methyl is commonly known as pyrimethanil, and wherein $R_{10}$ is cyclopropyl is commonly known as cyprodinil.

The specific compounds b) mentioned in the preceding paragraphs are commercially available. Other compounds falling under the scope of the various groups of component b) are obtainable according to procedures analogous to those known for preparing the commercially available compounds.

It has been found that the use of compounds of formula II in combination with the compound of formula I, particularly with one of the compounds penconazole, propiconazole, cyproconazole or difenoconazole surprisingly and substantially enhances the effectiveness of the latter against fungi, and vice versa. Additionally, the method of the invention is effective against a wider spectrum of such fungi that can be combatted with the active ingredients of this method when used solely.

Specific combinations according to present invention are: compound of formula I with a second fungicide selected from the group cyproconazole, hexaconazole, difenoconazole, etaconazole, propiconazole, tebuconazole, triticonazole, flutriafol, epoxiconazole, fenbuconazole, bromuconazole, penconazole, imazalil, tetraconazole, flusilazole, metconazole, dodemorph, tridemorph, fenpropimorph, spiroxamine, prochloraz, fenpropidine, dimethomorph, pyrimethanil and cyprodinil.

The most preferred combinations according to present invention are those of fenpropidine, penconazole, cyproconazole, or cyprodinil with the compound of formula I.

The weight ratio of a):b) is so selected as to give a synergistic fungicidal action. In general the weight ratio of a):b) is between 10:1 and 1:50. The synergistic action of the composition is apparent from the fact that the fungicidal action of the composition of a)+b) is greater than the sum of the fungicidal actions of a) and b).

Where the component b) is an azole fungicide of formula II the weight ratio of a):b) is for example between 10:1 and 1:10, especially 5:1 and 1:5, and more preferably 2:1 and 1:4.

Where the component b) is a morpholine fungicide of formula III the weight ratio of a):b) is for example between 1:1 and 1:10, especially 1:2 and 1:10, and more preferably 1:3 to 1:8.

Where component b) is the fungicide of formula IV, the weight ratio of a): b) is for example between 1:1 and 1:10, especially 1:2 and 1:10, and more preferably 1:3 and 1:8.

Where component b) is the fungicide of formula V, the weight ratio of a):b) is for example between 1:1 and 1:10, especially 1:2 and 1:10, and more preferably 1:3 and 1:8.

Where component b) is the fungicide of formula VI, the weight ratio of a): b) is for example between 1:1 and 1:20, especially 1:3 and 1:15, and more preferably 1:4 and 1:10.

Where component b) is the fungicide of formula VII, the weight ratio of a):b) is for example between 1:2 and 1:30, especially 1:3 and 1:20, and more preferably 1:5 to 1:15.

The method of the invention comprises applying to the treated plants or the locus thereof in admixture or separately, a fungicidally effective aggregate amount of a compound of formula I and a compound of component b).

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, germinated or soaked seeds.

The novel combinations are extremely effective on a broad spectrum of phytopathogenic fungi, in particular from the Ascomycetes and Basidiomycetes classes. Some of them have a systemic action and can be used as foliar and soil fungicides.

The fungicidal combinations are of particular interest for controlling a large number of fungi in various crops or their seeds, especially wheat, rye, barley, oats, rice, maize, lawns, cotton, soybeans, coffee, sugarcane, fruit and omamentals in horticulture and viticulture, and in vegetables such as cucumbers, beans and cucurbits.

The combinations are applied by treating the fungi or the seeds, plants or materials threatened by fungus attack, or the soil with a fungicidally effective amount of the active ingredients.

The agents may be applied before or after infection of the materials, plants or seeds by the fungi.

The novel combinations are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton, rice and lawns,
Ustilago species in cereals and sugarcane,
*Venturia inaequalis* (scab) in apples,
Helminthosporium species in cereals,
*Septoria nodorum* in wheat,
*Septoria tritici* in wheat wheat,
*Rhynchosporium secalis* on barley
*Botrytis cinerea* (gray mold) in strawberries, tomatoes and grapes,
*Cercospora arachidicola* in groundnuts,
*Pseudocercosporella herpotrichoides* (Tapesia spp.) in wheat and barley,
*Pyrenophera teres* in barley
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

When applied to the plants the compound of formula I is applied at a rate of 50 to 200 g/ha, particularly 75 to 150 g/ha, e.g. 75, 100, or 125 g/ha, in association with 50 to 1500 g/ha, particularly 60 to 1000 g/ha, e.g. 75 g/ha, 80 g/ha, 100 g/ha, 125 g/ha, 150 g/ha, 175 g/ha 200 g/ha, 300 g/ha, 500 g/ha, or 1000 g/ha of a compound of component b), depending on the class of chemical employed as component b). Where the component b) is an azole fungicide of formula II for example 50 to 300 g a.i./ha is applied in association with the compound of formula I. Where the component b) is a morpholine fungicide of formula III for example 250 to 500 g a.i./ha is applied in association with the compound of formula I. Where the component b) is the compound of formula IV for example 300 to 450 g a.i./ha is applied in association with the compound of formula I. Where the component b) is the compound of formula V for example 300 to 450 g a.i./ha is applied in association with the compound of formula I, where the component b) is the compound of formula VI for example 100 to 900 g a.i./ha is applied in association with the compound of formula I, where the component b) is the compound of formula VII for example 300 to 1200 g a.i./ha is applied in association with the compound of formula I, where the component b) is the compound of prochloraz for example 50 to 300 g a.i./ha is applied in association with the compound of formula I.

In agricultural practice the application rates depend on the type of effect desired, and range from 0.02 to 3 kg of active ingredient per hectare.

When the active ingredients are used for treating seed, rates of 0.001 to 50, and preferably from 0.01 to 10 g per kg of seed are generally sufficient.

The invention also provides fungicidal compositions comprising a compound of formula I and a compound of component b).

The composition of the invention may be employed in any conventional form, for example in the form of a twin pack, an instant granulate, a flowable or a wettable powder in combination with agriculturally acceptable adjuvants. Such compositions may be produced in conventional manner, e.g. by mixing the active ingredients with appropriate adjuvants (diluents or solvents and optionally other formulating ingredients such as surfactants).

Suitable carriers and adjuvants may be solid or liquid and correspond to the substances ordinarily employed in formulation technology, such as, e.g. natural or regenerated mineral substances, solvents, dispersants, wetting agents, tackifiers, thickeners, binding agents or fertilisers. Such carriers are for example described in WO 96/22690.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid adjuvant(s), the active agent consisting of at least thee compound of formula I together with a compound of component b), and optionally other active agents, particularly guazatin and fenpiclonil. Concentrate forms of compositions generally contain in between about 2 and 80%, preferably between about 5 and 70% by weight of active agent. Application forms of formulation may for example contain from 0.01 to 20% by weight, preferably from 0.01 to 5% by weight of active agent.

Examples for specific formulations-combination are as disclosed e.g. in WO 96/22690, e.g. for wettable powders, emulsifiable concentrate, dusts, extruder granules, coated granules, suspension concentrate.

Slow Release Capsule Suspension 28 parts of a combination of the compound of formula I and a compound of component b), or of each of these compounds separately, are mixed with 2 parts of an aromatic solvent and 7 parts of toluene diisocyanatelpolymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerisation reaction is completed.

The obtained capsule suspension is stabilized by adding 0.25 parts of a thickener and 3 parts of a dispersing agent. The capsule suspension formulation contains 28% of the active ingredients. The medium capsule diameter is 8–15 microns.

The resulting formulation is applied to seeds as an aqueous suspension in an apparatus suitable for that purpose.

Whereas commercial products will preferably be formulated as concentrates, the end user will normally employ dilute formulations.

BIOLOGICAL EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20–22; 1967):

ppm=milligrams of active ingredient (=a.i.) per liter of spray mixture

X=% action by active ingredient I using p ppm of active ingredient

Y=% action by active ingredient 11 using q ppm of active ingredient.

According to Colby, the expected (additive) action of active ingredients I+II using p+q ppm of active ingredient is $$E = X + Y - \frac{X \cdot Y}{100}$$

If the action actually observed (O) is greater than the expected action (E), then the action of the combination is superadditive, i.e. there is a synergistic effect.

Alternatively the synergistic action may also be determined from the dose response curves according to the so-called WADLEY method. With this method the efficacy of the a.i. is determined by comparing the degree of fungal attack on treated plants with that on untreated, similarly inoculated and incubated check plants. Each a.i. is tested at 4 to 5 concentrations. The dose response curves are used to establish the EC90 (i.e. concentration of a.i. providing 90% disease control) of the single compounds as well as of the combinations (EC $90_{observed}$). The thus experimentally found values of the mixtures at a given weight ratio are compared with the values that would have been found were only a complementary efficacy of the components was present (EC 90 (A+B)$_{expected}$). The EC90 (A+B)$_{expected}$ is calculated according to Wadley (Levi et al., EPPO-Bulletin 16, 1986, 651–657):

$$EC\ 90\ (A+B)_{expected} = \frac{a+b}{\frac{a}{EC90\ (A)_{observed}} + \frac{b}{EC90\ (B)_{observed}}}$$

wherein a and b are the weight ratios of the compounds A and B in the mixture and the indexes (A), (B), (A+B) refer to the observed EC 90 values of the compounds A, B or the given combination A+B thereof. The ratio EC90 (A+B)$_{expected}$/EC90 (A+B)$_{observed}$ expresses the factor of interaction (F). In case of synergism, F is >1.

EXAMPLE B-1

Residual-protective Action Against *Venturia inaegualis* on Apples

Apple cuttings with 10–20 cm long fresh shoots are sprayed to drip point with an aqueous spray mixture prepared from a wettable powder formulation of the active ingredient mixture and infected 24 hours later with a conidia suspension of the fungus. The plants are incubated for 5 days at 90–100% relative humidity and stood in a greenhouse for a further 10 days at 20–24° C. Fungus infestation is evaluated 12 days after infection.

EXAMPLE B-2

Action Against *Botrytis cinerea* on Apple Fruits

Artificially damaged apples are treated by dropping a spray mixture of the active ingredient mixture onto the damage sites. The treated fruits are then inoculated with a spore suspension of the fungus and incubated for one week at high humidity and about 20° C. The fungicidal action of the test compound is derived from the number of damage sites that have begun to rot.

EXAMPLE B-3

Action Against *Podosphaera leucotricha* on Apple Shoots

Apple cuttings with about 15 cm long fresh shoots are sprayed with a spray mixture of the active ingredient mixture. The treated plants are infected 24 hours later with a conidia suspension of the fungus and placed in a climatic chamber at 70% relative humidity and 20° C. Fungus infestation is evaluated 12 days after infection.

EXAMPLE B-4

Action Against *Drechslera teres* on Barley 10-day-old barley plants of the "Golden Promise" variety are sprayed with a spray mixture of the active ingredient mixture. The treated plants are infected 24 hours later with a conidia suspension of the fungus and incubated in a climatic chamber at 70% relative humidity and 20–22° C. Fungus infestation is evaluated 5 days after infection.

EXAMPLE B-5

Efficacy Against *Erysiphe graminis* f.sp. *tritici* on Wheat

Five to ten wheat seeds c.v. "Arina" are sown in plastic pots of 7 cm diameter and grown for 7 to 12 days at 20° C., 50–70% rH. When the primary leaves have fully expanded, the plants are spray treated with aqueous spray liquors containing the single compounds, or mixtures thereof (hereinafter a.i.). All compounds are used as experimental or commercially available formulations, combinations are applied as tank mixtures. The application comprises foliar spraying to near runoff (three pots per treatment). 24 hours after the application or 24 hours before application, the plants are inoculated in a settling tower with fresh spores of *Erysiphe graminis* f. sp. *tritici*. The plants are then incubated in a growth chamber at 20° C., 60% rH. Seven days after the inoculation, the percentage of infection on primary leaves is evaluated. The efficacy of the a.i. is determined by comparing the degree of fungal attack on treated plants with that on untreated, similarly inoculated and incubated check plants. Each a.i. is tested at 4 to 5 concentrations. The synergie factor is calculated according to the COLBY method.

Results:

TABLE 1

| curative application | | | | | | | | |
|---|---|---|---|---|---|---|---|---|
| Quino-xyfen mg a.i./l | Cypro-dinil mg a.i./l | Cyproco-nazole mg a.i./l | Propico-nazole mg a.i./l | Fenpro-pidin mg a.i./l | Ratio | % activity observed | % activity expected | SF Colby |
| 0.05 | | | | | | 1 | | |
| 0.1 | | | | | | 3 | | |
| 0.25 | | | | | | 6 | | |
| 0.5 | | | | | | 4 | | |
| 1 | | | | | | 7 | | |
| | 25 | | | | | 25 | | |
| | | 0.05 | | | | 7 | | |
| | | 0.1 | | | | 8 | | |
| | | 0.25 | | | | 16 | | |
| | | 0.5 | | | | 24 | | |
| | | | 0.1 | | | 34 | | |
| | | | | 0.05 | | 0 | | |
| 1 | 25 | | | | 1:25 | 41 | 30 | 1.4 |
| 0.05 | | 0.05 | | | 1:1 | 17 | 8 | 2.2 |
| 0.05 | | 01 | | | 1:2 | 15 | 9 | 1.6 |
| 0.05 | | 0.25 | | | 1:5 | 25 | 17 | 1.5 |
| 0.1 | | 0.05 | | | 2:1 | 16 | 10 | 1.6 |
| 0.1 | | 0.1 | | | 1:1 | 21 | 11 | 1.9 |
| 0.1 | | 0.5 | | | 1:5 | 37 | 26 | 1.4 |
| 0.25 | | 0.25 | | | 1:1 | 30 | 21 | 1.4 |

TABLE 1-continued curative application

| Quinoxyfen mg a.i./l | Cyprodinil mg a.i./l | Cyproconazole mg a.i./l | Propiconazole mg a.i./l | Fenpropidin mg a.i./l | Ratio | % activity observed | % activity expected | SF Colby |
|---|---|---|---|---|---|---|---|---|
| 0.25 |  | 0.5 |  |  | 1:2 | 48 | 29 | 1.7 |
| 0.5 |  | 0.25 |  |  | 2:1 | 40 | 20 | 2 |
| 0.5 |  | 0.5 |  |  | 1:1 | 58 | 27 | 2.2 |
| 0.05 |  |  | 0.1 |  | 1:2 | 48 | 35 | 1.3 |
| 0.05 |  |  |  | 0.05 | 1:1 | 40 | 1 | 40 |

TABLE 2 protective application

| Quinoxyfen mg a.i./l | Cyproconazole mg a.i./l | Propiconazole mg a.i./l | Fenpropidin mg a.i./l | Ratio | % activity observed | % activity expected | SF Colby |
|---|---|---|---|---|---|---|---|
| 0.05 |  |  |  |  | 0 |  |  |
| 0.1 |  |  |  |  | 1 |  |  |
| 0.25 |  |  |  |  | 3 |  |  |
|  | 0.05 |  |  |  | 1 |  |  |
|  | 0.1 |  |  |  | 2 |  |  |
|  | 0.25 |  |  |  | 4 |  |  |
|  | 0.5 |  |  |  | 12 |  |  |
|  |  | 0.1 |  |  | 1 |  |  |
|  |  | 0.25 |  |  | 12 |  |  |
|  |  |  | 0.5 |  | 2 |  |  |
| 0.05 | 0.25 |  |  | 1:5 | 7 | 4 | 1.5 |
| 0.1 | 0.05 |  |  | 2:1 | 6 | 2 | 3 |
| 0.1 | 0.1 |  |  | 1:1 | 11 | 3 | 3.6 |
| 0.1 | 0.25 |  |  | 1:2,5 | 16 | 5 | 3.2 |
| 0.1 | 0.5 |  |  | 1:5 | 17 | 13 | 1.3 |
| 0.25 | 0.1 |  |  | 2,5:1 | 14 | 5 | 2.8 |
| 0.25 | 0.25 |  |  | 1:1 | 12 | 7 | 1.7 |
| 0.05 |  | 0.1 |  | 1:2 | 11 | 1 | 11 |
| 0.05 |  | 0.25 |  | 1:5 | 23 | 12 | 1.9 |
| 0.05 |  |  | 0.5 | 1:10 | 4 | 2 | 2 |

EXAMPLE B-6

Field Test on *Erysiphe graminis*

A field trial was carried out in Germany with winter wheat, cv.Kanzler. The experiment was arranged with 4 replicates in randomized plots of 12.5 m². Cyproconazole was used as a EC240, quinoxyfen as a SC500 and the mixture cyproconazole/quinoxyfen as a SC155 formulation. Cyproconazole was applied at 80 g a.i./ha, quinoxyfen at 75 g a.i./ha and the mixture contained the same amounts of the individual active ingredients. The spray volume of all treatments was 400 l/ha. Disease assessment of *Erysiphe graminis* was estimated 29 days after application when untrated control plants had 15% infected leaf area. Results are expressed as % activity calculated on the basis of % infected leaf area. Result:

|  | concentration | % infested leaf area after 29 days | % activity observed | % activity expected | SF Colby |
|---|---|---|---|---|---|
| control (untreated) |  | 15 |  |  |  |
| Cypro- | SL100 | 6 | 60 |  |  |
| conazole | 80 g a.i./ha |  |  |  |  |
| Quinoxyfen | SC500 75 g a.i./ha | 10 | 33 |  |  |
| Mixture | SC155 155 g a.i./ha | 2 | 87 | 73 | 1.2 |

EXAMPLE B-7

Activity Against *Uncinula necator*

Grape plants, 4 weeks old (4–5 leaves), are sprayed to near run off with a suspension containing 250 mg/l of active ingredient. The deposit is then allowed to dry. One day later, the treated plants are inoculated by dusting freshly harvested conidia over the test plants; then the plants were incubated in a growt chamber for 10–14 days at +22° C. and 70% r.h. The efficacy of the test compounds is determined by comparing the degree of fungal attack with that on untreated, similarly inoculated check plants. I The mixtures according to the invention exhibit good activity in these Examples.

TABLE 3

| Quinoxylen mg a.i./l | Penconazole mg a.i./l | Ratio | % activity observed | % activity expected | SF COLBY |
|---|---|---|---|---|---|
| 0.1 | | | 48 | | |
| 1 | | | 58 | | |
| | 0.1 | | 7 | | |
| | 1 | | 42 | | |
| 0.1 | 0.1 | 1:1 | 60 | 52 | 1.2 |
| 1 | 1 | 1:1 | 88 | 76 | 1.2 |
| 1 | 0.1 | 10:1 | 83 | 61 | 1.4 |

EXAMPLE B-8

Activity Against Septoria (Field Trial)

A field trial was carried out in Great Britain with winter wheat, cv. Consort. The experiment was arranged with 4 replicates in randomized plots each of 36 m². Application was carried out at 5–10% infected leaf area on the lower leaves. Cyproconazole was used as a EC240, quinoxyfen as a SC500 and the mixture cyproconazole/quinoxyfen as a SC155 formulation. Cyproconazole was applied at 80 g a.i./ha, quinoxyfen at 75 g a.i./ha and the mixture contained the same amounts of the individual active ingredients. The spray volume of all treatments was 200 l/ha. Disease assessment of Septoria spp. was estimated 84 days after application when the untrated control plants had approximated 97% infected leaf area. Results are expressed as % activity calculated on the basis of % infected leaf area. Result:

| | concentration | % infested leaf after 84 days | % activity observed | % activity expected | SF Colby |
|---|---|---|---|---|---|
| control (untreated) | | 97 | | | |
| Cyproconazole | EC240 80 g a.i./ha | 56 | 42 | | |
| Quinoxyfen | SC500 75 g a.i./ha | 85 | 12 | | |
| Mixture | SC155 155 g a.i/ha | 38 | 61 | 49 | 1.2 |

What is claimed is:

1. A method of combating phytopathogenic diseases on crop plants which comprises applying to the crop plants or to the locus thereof being infested with said phytopathogenic disease a synergistic fungicidally effective amount of a combination of a) a 4-phenoxyquinoline of formula I

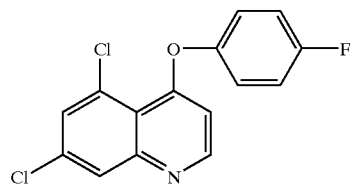

(I)

in association with b) fenpropidin and wherein the weight ratio of a) to b) is from 10:1 to 1:50.

2. A fungicidal composition comprising synergistic fungicidafly effective amounts of a) a 4-phenoxyquinoline of formula I

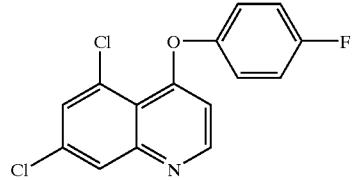

(I)

in association with b) tenpropidin;

and wherein the weight ratio of a) to b) is from 10:1 to 1:50.

* * * * *